United States Patent [19]

Gruber et al.

[11] Patent Number: 4,780,526

[45] Date of Patent: Oct. 25, 1988

[54] COMPOSITION, METHOD FOR PREPARING AND USE THEREOF

[75] Inventors: Bruce A. Gruber, Delaware; Heimo J. Langer; William R. Dunnayant, both of Franklin, all of Ohio

[73] Assignee: Ashland Oil, Inc., Ashland, Ky.

[21] Appl. No.: 918,178

[22] Filed: Oct. 14, 1986

Related U.S. Application Data

[60] Division of Ser. No. 722,498, Apr. 12, 1985, Pat. No. 4,636,537, which is a continuation-in-part of Ser. No. 575,254, Jan. 30, 1984, Pat. No. 4,529,771, which is a continuation-in-part of Ser. No. 524,050, Aug. 16, 1983, Pat. No. 4,483,961, which is a continuation-in-part of Ser. No. 300,786, Sep. 10, 1981, Pat. No. 4,412,088.

[51] Int. Cl.$^4$ .............. C08G 16/02; C08L 61/00

[52] U.S. Cl. .................. 528/239; 523/139; 523/144; 523/145; 526/208

[58] Field of Search .............. 523/139, 144, 145; 168/139; 526/123, 208; 528/239

[56] References Cited

U.S. PATENT DOCUMENTS 4,483,961 11/1984 Koch et al. .............. 523/139
4,529,771 7/1985 Gruber et al. .............. 523/139

Primary Examiner—Allan M. Lieberman
Attorney, Agent, or Firm—Pollock, Vande Sande & Priddy

[57] ABSTRACT

Polymeric cyclopentadiene derivatives, method for preparing polymeric cyclopentadiene derivatives, and use of polymeric cyclopentadiene derivatives in curable binder compositions.

7 Claims, No Drawings

COMPOSITION, METHOD FOR PREPARING AND USE THEREOF

This is a divisional of application Ser. No. 722,498, filed on Apr. 12, 1985, now U.S. Pat. No. 4,636,537 which application is a continuation-in-part of our copending U.S. patent application Ser. No. 575,254, filed on Jan. 30, 1984 and entitled "Composition, Method for Preparing and Use Thereof", now U.S. Pat. No. 4,529,771, which, in turn, is a continuation-in-part of U.S. patent application Ser. No. 524,050, filed on Aug. 16, 1983 and entitled "Polymeric Cyclopentadiene Derivatives, Method for Preparing and Use Thereof", now U.S. Pat. No. 4,483,961, which, in turn, is a continuation-in-part of U.S. patent application Ser. No. 300,786, filed on Sept. 10, 1981 and entitled "Cyclopentadiene Derivatives, Method for Preparing and Use Thereof", now U.S. Pat. No. 4,412,088; disclosures of which are incorporated herein by reference.

DESCRIPTION

1. Technical Field

The present invention is directed to new polymeric cyclopentadiene derivatives which are particularly useful in binder compositions. Such compositions are curable to a thermoset state at normal room temperatures and at elevated temperatures. The compositions are capable of being cured at normal room temperatures by a gaseous curing agent or an acidic catalyst incorporated into the binder. Derivatives of the present invention are also capable of being crosslinked with polyisocyanates. The compositions of the present invention are especially useful as foundry binders The present invention is also directed to a method for preparing the polymeric derivatives of cyclopentadiene.

2. Background Art

In the foundry art, cores and molds used in making metal castings are generally prepared from shaped, cured mixtures of aggregate material (e.g. sand) and a binder. One of the preferred techniques of making these sand cores includes the basic steps of mixing the sand with a resin binder and a curing catalyst, molding the mixture to the desired shape and allowing it to cure and solidify at room temperature without the application of heat. Resins useful in this technique include furfuryl alcohol-formaldehyde polymers, furfuryl alcohol-urea-formaldehyde polymers, alkyd isocyanate resins, and sodium silicate binders. Such technique is commonly referred to as a "no bake" process.

Another preferred technique employed includes the basic steps of mixing the aggregate with a resin binder, molding the mixture to the desired shape, and curing the shape by passing a gaseous catalyst through it. This technique is often referred to as the "cold box" method.

Another technique employed is referred to as the "warm box" method which involves the use of elevated temperatures such as from about 225° F. to about 500° F. to effect curing of the binder.

Binders which are suitable for use in such processes must possess a number of important characteristics. For instance, the binders must be capable of providing relatively high strength characteristics to the molded article and must be capable of curing to a considerable degree at normal room temperatures to be for the "no bake" and "cold box" methods.

Also, since curing of the binders occurs while as a thin layer of film on the aggregate and the aggregate can act as a heat sink, the curing does not necessarily proceed in the same manner as when the binder is cured in bulk. In addition, foundry cores and molds must retain the strength properties until the metal solidifies in the mold, but must lose such properties due to their exposure at higher temperatures so that after solidification of the metal, the cores or molds can readily be broken down for shake-out or removal from the casting. Accordingly, providing new binders for foundry applications which contain the necessary properties is quite difficult. This problem is made more acute when the object is a relatively inexpensive binder.

It has also been discovered that fulvenes and/or fulvene prepolymers could be employed as binders for foundry applications as described in U.S. Pat. No. 4,246,167 to Grimm, et al., entitled "Foundry Binder Composition" and assigned to Ashland Oil, Inc., the assignee of the present application. However, the use of such fulvenes has not been entirely satisfactory since such are somewhat susceptible to degradation from atmospheric oxygen and have an unpleasant odor.

In addition, in U.S. Pat. No. 4,246,167, certain derivatives of cyclopentadiene and/or of methyl cyclopentadiene which have improved resistance to atmospheric oxygen and reduced odor as compared to the fulvenes discussed hereinabove are disclosed.

In U.S. Pat. No. 4,483,961, polymeric cyclopentadiene derivatives which have greater erosion resistance when compared to the use of the fulvenes and cyclopentadiene derivatives mentioned above are disclosed.

SUMMARY OF INVENTION

The present invention is concerned with novel polymeric derivatives of cyclopentadiene and/or of methyl substituted cyclopentadiene.

Also provided according to the present invention is a process for preparing certain, polymeric derivatives of cyclopentadiene and/or of methyl substituted cyclopentadiene.

The present invention is also concerned with the use of certain polymeric derivatives of cyclopentadiene and/or of methyl substituted cyclopentadiene in binder compositions and especially foundry binder compositions.

The polymers of the present invention in the absence of catalyst have increased resistance to premature polymerization due to oxygen such as atmospheric oxygen.

Moreover, the present invention makes it possible to provide polymers which are curable by a variety of techniques.

Also, the polymers of the present invention have reduced odor as compared to the fulvenes and the cyclopentadiene derivatives discussed hereinabove, and including those disclosed in copending application Ser. No. 575,254. Moreover, the polymers of the present invention, when used in a binder composition for molded articles, demonstrate substantially no erosion tendency.

Moreover, the polymers of the present invention, when used in a binder composition for foundry shapes, provide for good surface finishing of the metal case in the foundry shape. Furthermore, reduced smoke has been observed in iron castings employing foundry shapes with the polymers of the present invention.

The present invention is concerned with polymeric cyclopentadiene derivatives having recurring units of the immediate following Formula I, or isomers thereof, or mixtures thereof:

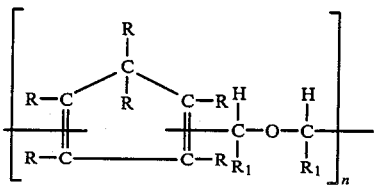

Each R, other than the R group(s) which act as the

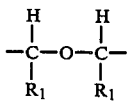

linkage between adjacent recurring units, individually is hydrogen, methyl,

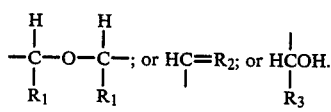

Each $R_1$, individually, is hydrogen or an alkyl group having 1-4 carbon atoms. $R_2$ is methylene or ethylidene. $R_3$ is hydrogen, methyl, or ethyl. At least three (3) of the R groups are hydrogen. At least two (2) of the R groups attached to different carbon atoms is

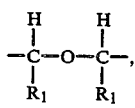

except when n is 2, then at least one of the R groups is

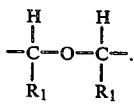

In addition, n is an integer of at least 2.

The present invention is also concerned with a curable composition which includes at least one polymeric cyclopentadiene derivative of the type discussed hereinabove and an acidic catalyst. The acidic catalyst has a pKa of about 4 or less and is considered a proton donor. The acidic catalyst is incorporated into the composition prior to molding or is provided by passing a gas through the molded composition.

The present invention is also concerned with a curable composition which includes at least one polymeric cyclopentadiene derivative of the type discussed hereinabove and an organic polyisocyanate.

The present invention is also concerned with molding compositions which include a major amount of aggregate and an effective bonding amount up to about 40% by weight of the aggregate of the above-defined curable compositions The present invention is also directed to a process for the fabrication of molded articles which includes the following steps:

(a) mixing aggregate with a bonding amount up to about 40% by weight based upon the weight of the aggregate of binder compositions of the type described hereinabove;

(b) introducing the composition obtained from step (a) into a pattern;

(c) hardening the composition in the pattern to become self-supporting; and (d) thereafter, removing the shaped article of step (c) from the pattern and allowing it to further cure, thereby obtaining a hardened, solid, cured, molded article.

The present invention is also concerned with a process for casting a metal which includes fabricating a shape as described hereinabove, pouring metal while in the liquid state into or around the shape, allowing the metal to cool and solidify, and then separating the molded metal article.

The present invention is also concerned with a process for preparing a polymeric cyclopentadiene derivative which comprises reacting cyclopentadiene or methyl cyclopentadiene, or both, with an aldehyde having 1-5 carbon atoms in the presence of about 0.004 to about 0.007 moles of a basic catalyst per mole of cyclopentadiene, methyl cyclopentadiene, or both, to provide a polymeric cyclopentadiene derivative.

The reaction is usually carried out at a temperature of about 20° C. to about 40° C. The reaction is usually completed in about 4 hours to about 12 hours.

Moreover, the present invention is directed to polymeric cyclopentadiene derivatives obtained by the process described hereinabove.

BEST AND VARIOUS MODES FOR CARRYING OUT THE INVENTION

The polymeric cyclopentadiene derivatives of the present invention are represented by the recurring Formula I below, or isomers, or mixtures thereof:

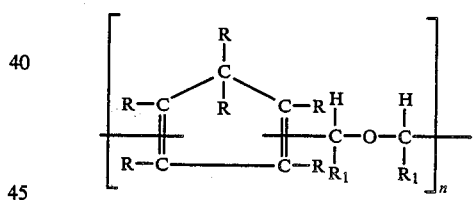

Each R, other than the R group(s) which act as the

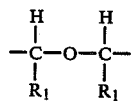

linkage between adjacent recurring units, individually is hydrogen, methyl,

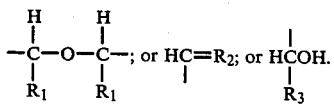

Each $R_1$, individually, is hydrogen or an alkyl group having 1-4 carbon atoms, and preferably is hydrogen or methyl, and most preferably in hydrogen. $R_2$ is methylene or ethylidene. $R_3$ is hydrogen, methyl, or ethyl and preferably is hydrogen. At least three (3) of the R groups are hydrogen. At least two (2) of the R groups on different carbon atoms is

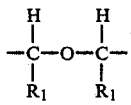

except when n is 2, then at least one of the R groups is

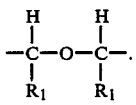

In the above Formula I, n is at least 2 and usually 2 to about 20, preferably 2 to about 10, and most preferably about 3 to about 6.

Polymeric derivatives within the scope of the present invention can be prepared by reacting cyclopentadiene, or methyl cyclopentadiene, or both, with an aldehyde containing 1-5 carbon atoms. The preferred aldehydes are formaldehyde and acetaldehyde with formaldehyde being most preferred.

The reaction is carried out in the presence of about 0.004 to about 0.007 moles of a basic catalyst per mole of cyclopentadiene, or methyl cyclopentadiene, or both. If the amounts of catalyst employed is significantly greater than that discussed above, the product obtained will not contain the type of ether linkages as required by the present invention

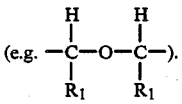

Examples of some basic catalysts include: strong bases (e.g. KOH), amines, and basic ion exchange resins. This reaction is generally carried out at temperatures of about 20° C. to about 40° C. Generally, about 0.1 to about 2.5 moles of aldehyde and preferably about 0.5 to about 2 moles of aldehyde are employed for each mole of cyclopentadiene and/or methyl cyclopentadiene. This reaction is preferably carried out in an alcoholic solution. Examples of alcohols are methyl alcohol, ethyl alcohol, isopropyl alcohol, and furfuryl alcohol. The reaction usually takes about 4 to about 24 hours. The reaction is usually carried out under atmospheric pressure. However, higher or lower pressures can be used if desired.

When the aldehyde employed is formaldehyde, such is preferably employed as paraformaldehyde. Paraformaldehyde is a substantially water-free source of formaldehyde and is a mixture of polyoxymethylene glycol which usually contains from about 90% to about 99% by weight of formaldehyde with the balance consisting principally of free and combined water as long as the mixture is still a solid material. Usually, commercial grades of paraformaldehyde contain from about 91% to about 98% formaldehyde. The chemical composition of paraformaldehyde can be expressed by the following formula:

wherein n is equal to 8 to 100. Normally, the majority of the polyoxymethylene glycols in paraformaldehyde contain over about 12 formaldehyde units per molecule. Paraformaldehyde has a melting point of from about 120° C. to about 170° C.

Of course, other forms capable of supplying formaldehyde to the reaction mass, such as formaldehyde, per se, formaldehyde in the form of an alcoholic solution such as a methanol solution, and trioxane can be used.

The existence of

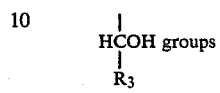

in the polymer depends upon reaction conditions and particularly the degree of dehydration of the product which occurs.

By following the above procedures, polymeric derivatives of the present invention, which are thermosetting, are obtained. The polymeric qerivatives have molecular weights up to about 2000 and n in structure I is an integer up to about 20. The polymeric derivatives preferably have average molecular weights of about 20 to about 1000, and preferably the average n in Formula I is an integer of about 2 to about 10.

The polymers preferably are fluid enough so that such, when applied either per se, or in admixture with the diluents, flow to coat the aggregate used.

The polymeric derivatives obtained in accordance with the present invention are lighter in color than the polymeric derivatives prepared according to the above-discussed prior patent applications and patents.

It should be further noted that by identifying the polymeric derivative according to Formula I is not intended to imply that materials having other structures are completely absent from the composition.

The polymeric cyclopentadiene derivatives of the present invention are especially useful in binder compositions and particularly foundry binder compositions. Mixtures of the polymeric cyclopentadiene derivatives can be used.

The polymers of the present invention demonstrate considerable resistance to elevated temperatures and to erosion during casting when employed in a foundry shape.

Furthermore, reduced smoke formation in iron castings has been observed durnng the casting of iron. The polymers of the present invention also exhibit reduced odor.

In addition, the binder composition of the present invention contains a catalyst or curing agent.

One particular type of catalyst is an acidic catalyst. The acidic catalysts employed have a pKa value of about 4 or less, and are proton donors, and include organic acids such as formic acid, oxalic acid, and the organic substituted sulfonic acids such as benzenesulfonic acid and toluenesulfonic acid, and Lewis acids such as BF$_3$. The preferred acidic catalysts are the organic substituted sulfonic acids. The acidic catalyst can be provided in the foundry mix before molding (e.g. "no bake" and "warm box" processes) and/or by passing a gas through the molded composition such as an acid, per se, or a gas such as SO$_2$ which, in conjunction with a component of the molded composition (e.g. a peroxide), forms an acid in situ.

The acidic catalyst, when already in the mix, prior to molding, is generally present in amounts up to a maximum of about 25% by weight based upon the amount of binder employed. The minimum amount of acidic catalyst is usually about 4% based upon the amount of binder employed. When employing a "cold box" process, usually up to about 5 seconds of gassing time is sufficient.

Furthermore, binder compositions of the present invention can be used in a "warm box" process at temperatures of about 300° F. to about 400° F.

Polymeric cyclopentadiene derivatives of the present invention and particularly those having terminal

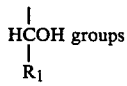

HCOH groups
  |
  $R_1$ are also curable to thermosetting materials by reaction with organic polyisocyanates.

The useful isocyanates comprise aliphatic, cycloaliphatic, or aromatic polyisocyanates having preferably from 2 to 5 isocyanate groups. If desired, mixtures of polyisocyanates can be employed. Less preferably, isocyanate prepolymers formed by reacting excess polyisocyanate with a polyhydric alcohol (e.g. a prepolymer of toluene diisocyanate and ethylene glycol) can be employed. Suitable polyisocyanates include the aliphatic polyisocyanates such as hexamethylene diisocyanate, alicyclic polyisocyanates such as 4,4'-dicyclohexylmethane diisocyanate, and aromatic polyisocyanates such as 2,4-and 2,6-toluene diisocyanate, diphenylmethyl diioscyanate, and the dimethyl derivatives thereof. Further examples of suitable polyisocyanates are 1,5-naphthalene diisocyanate, triphenylmethane triisocyanate, xylylene diisocyanate, and the methyl derivatives thereof, polymethylenepolyphenol isocyanates, chlorophenylene-2,4-diisocyanate, and the like.

The preferred polyisocyanates are aromatic polyisocyanates and particularly diphenylmethane diisocyanate, triphenylmethane triisocyanate, complex commercially available compositions containing polymeric isocyanates sold under such trademarks as "PAPI", "Mondur MR", and "NCO-120", and mixtures thereof.

In general, the polyisocyanate will be employed in a range of about 10 to about 500 weight percent of polyisocyanate based on the weight of the polymeric cyclopentadiene derivative. Preferably, from 20 to 300 weight percent of polyisocyanate on the same basis is employed. The polyisocyanate is employed in liquid form. Liquid polyisocyanates can be employed in undiluted form. Solid or viscous polyisocyanates are most conveniently employed in the form of organic solvent solutions, the solvent being present in arange of up to 80% by weight of the solution.

The curing can be facilitated by employing, in addition to the polyisocyanate, a tertiary amine and/or a base having a pKb value of about 4 to about 11. Preferably the tertiary amine is a liquid such as triethyl amine.

Although ammonia, primary amines, and secondary amines exhibit some activity in causing a room temperature reaction, they are considerably inferior to the tertiary amines. Functionally, substituted amines such as dimethyl ethanol amines are included within the scope of tertiary amines and can be employed as curing agents. Functional groups which do not interfere in the action of the tertiary amine are hydroxyl groups, alkoxy groups, amino and alkyl amino groups, ketoxy groups, thio groups, and the like.

The base catalysts having a pKb value of about 7 to about 11 are generally organic compounds containing one or more nitrogen atoms. Preferred materials are heterocyclic compounds containing at least one nitrogen atom in the ring structure. Specific examples of bases which have pKb values within the necessary range include 4-alkyl pyridines wherein the alkyl group has from 1 to 4 carbon atoms, isoquinoline, aryl-pyridines such as phenyl pyridine, pyridine, acridine, 2-methoxypyridine, pyridazine, 3-chloro pyridine, quinoline, N-methyl imidazole, 4,4-dipyridine, phenylpropyl pyridine, 1-methyl-benzimidazole, and 1,4-thiazine.

In view of the varying catalytic activity and varying catalytic effect desired, catalyst concentrations will vary widely. In general, the lower the pKb value is, the shorter will be the low reactivity interval of the composition and the faster, more complete will be the cure. Solvents and any acidity present in added ingredients such as sand may effect the catalytic activity. In general, however, catalyst concentrations will range from 0.01% to 10% by weight of the polymeric cyclopentadiene.

The polymeric cyclopentadiene derivatives can be employed in combination with fulvenes of the type discussed hereinabove, and/or with disubstituted cyclopentadiene derivatives, and/or prepolymers thereof, as discussed in U.S. Pat. No. 4,412,088, and/or with other polymeric cyclopentadiene derivatives such as those disclosed in U.S. patent application Ser. No. 575,254 and U.S. Pat. No. 4,483,961, and/or with furfuryl alcohol, and/or furan prepolymer foundry binder systems, and/or phenolic materials such as phenol, substituted phenols, or phenolformaldehyde condensates.

The furan prepolymers include reaction products of furfuryl alcohol and of aldehydes such as formaldehyde. In addition, the aldehyde-furfuryl alcohol reaction product can be modified with varying amounts of reactants such as urea. The mole ratios of formaldehyde to furfuryl alcohol which can be employed can vary widely. For instance, the furan polymer can be prepared from about 0.4 to about 4 moles of furfuryl alcohol per mole of formaldehyde, and preferably from about 0.5 to about 2 moles of furfuryl alcohol per mole of formaldehyde.

The furan polymer which can be employed in the present invention can be any of the various furan polymers which are known to be suitable for molding and especially foundry purposes. Examples of such furan polymers include those obtained from about 1 mole of urea, about 0.2 to 2 moles of furfuryl alcohol, and about 1 to 3 moles of formaldehyde such as described in U.S. Pat. Nos. 3,222,315 and 3,247,556. Other suitable furan polymers are disclosed in U.S. Pat. No. 3,346,534. The furan polymers are usually prepared by polymerization in the presence of an acid catalyst. Usually, when a furan polymer is employed, it is added together with furfuryl alcohol.

When the polymeric cyclopentadiene derivatives of the present invention are employed in admixture with other materials of the type discussed above, as auxiliary binders, such as furfuryl alcohol and/or other polymeric cyclopentadiene derivatives, and/or disubstituted cyclopentadiene derivatives, and/or fulvenes, and/or furan polymers, and/or phenolics, such polymeric cyclopentadiene derivatives are generally employed in amounts of about 90% to about 10% by weight based upon the total amount of polymeric cyclopentadiene derivative of the present invention and other materials defined above.

In addition, the compositions can contain a dialkyl ester of the formula:

$$R_1OOC(CH_2)_nCOOR_2$$

wherein each $R_1$ and $R_2$, individually is an alkyl of 1 to 20 carbon atoms and n is a whole number integer of 0 to 4. The ester may be blended with the binder and/or sand and/or in conjunction with the catalyst. Suitable esters include dimethyl oxalate, diethyl oxalate, dimethyl succinate, methyl-ethyl succinate, methyl-n-propyl succinate, methyl isopropyl succinate, methyl-n-butyl succinate, diethyl succinate, ethyl-n-propyl succinate, diisopropyl succinate, dibutyl succinate, dimethyl glutarate, methylethyl glutarate, methyl-n-butyl glutarate, methyl-isobutyl glutarate, diethyl glutarate, ethyl-n-propyl glutarate, diisopropyl glutarate, dibutyl glutarate, dimethyl adipate, methylethyl adipate, ethyl-n-propyl adipate, methylisopropyl adipate, diethyl adipate, dipropyl adipate, dibutyl adipate, dioctyl succinate, dioctyl adipate, dicapryl adipate, dicapryl ,succinate, dicapryl glutarate, dilauryl adipate, dilauryl succinate, dilauryl glutarate, and malonic acid esters.

Preferred esters are the oxalates; dimethyl glutarate such as available from DuPont under the trade designation DBE-5; dimethyl adipate available from DuPont under the trade designation DBE-6; and mixtures of such esters such as are available from DuPont under the trade designation DBE. Other diluents can be employed if desired and include such groups of compounds as ketones such as acetone, methylethyl ketone, and diisoamylketone; ketoacid esters such as ethyl acetoacetate and methyl acetoacttate; and other esters such as the cellosolve esters.

The diluent may generally be employed in an amount of from about 0.5% to 55% and preferably 10% to 40% by weight of the binder.

When preparing an ordinary sand-type foundry shape, the aggregate employed has a particle size large enough to permit sufficient porosity in the foundry shape to permit escape of volatiles from the shape during the casting operation. The term "ordinary sand-type foundry shapes" as used herein, refers to foundry shapes which have sufficient porosity to permit escape of volatiles from it during the casting operation. Generally, at least about 80% and preferably about 90% by weight of aggregate employed for foundry shapes has an average particle size no smaller than about 150 mesh (Tyler screen mesh). The aggregate for foundry shapes preferably has an average particle size between about 50 and about 150 mesh (Tyler screen mesh). The preferred aggregate employed for ordinary foundry shapes is silica sand wherein at least about 70 weight percent and preferably at least about 85 weight percent of the sand is silica. Other suitable aggregate materials include zircon, olivine, aluminosilicate sand, chromite sand, and the like.

When preparing a shape for precision casting, the predominant portion and generally, at least about 80% of the aggregate, has an average particle size no larger than about 150 mesh (Tyler screen mesh). Preferably, at least about 90% by weight of the aggregate for precision casting applications has a particle size no larger than 150 mesh and preferably between 325 mesh and 200 mesh. The preferred aggregates employed for precision casting applications are fused quartz, zircon sands, magnesium silicate sands, such as olivine and aluminosilicate sands.

Shapes for precision casting differ from ordinary sand-type foundry shapes in that the aggregate in shapes for precision casting can be more densely packed than the aggregate in shapes for ordinary sand-type foundry shapes. Therefore, shapes for precision casting must be heated before being utilized to drive off volatazable material present in the molding composition. If the volatiles are not removed from a precision casting shape before use, vapor created during casting will diffuse into the molten melt, since the shape has a relatively low porosity. The vapor diffusion would decrease the smoothness of the surface of the precision cast article.

When preparing a refractory such as ceramic, the predominant portion and at least about 80% by weight of the aggregate employed has an average particle size under 200 mesh and preferably no larger than 325 mesh. Preferably at least about 90% by weight of the aggregate for a refractory has an average particle size under 200 mesh and preferably no larger than 325 mesh. The aggregate employed in the preparation of refractories must be capable of withstanding the curing temperatures such as above about 1500° F. which are needed to cause sintering for utilization.

Examples of some suitable aggregate employed for preparing refractories include the ceramics such as refractory oxides, carbides, nitrides; and silicides such as aluminum oxide, lead oxide, chromic oxide, zirconium oxide, silica, silicon carbide, titanium nitride, boron oxide, boron nitride, molybdenum disilicide; and carbonaceous material such as graphite. Mixtures of the aggregates can also be used, when desired, including mixtures of metals and the ceramics.

Examples of some abrasive grains for preparing abrasive articles include aluminum oxide, silicon carbide, boron carbide, corundum, garnet, emery, and mixtures thereof. The grit size is of the usual grades as graded by the U.S. Bureau of Standards. These abrasive materials and their uses for particular jobs are understood by persons skilled in the art and are not altered in the abrasive articles contemplated by the present invention. In addition, inorganic filler can be employed along with the abrasive grit in preparing abrasive articles. It is preferred that at least about 85% of the inorganic fillers has an average particle size no greater than 200 mesh. It is most preferred that at least about 95% of the inorganic filler has an average particle size no greater than 200 mesh. Some inorganic fillers include cryolite, fluorospar, silica, and the like. When an organic filler is employed along with the abrasive grit, it is generally present in amounts from about 1 to about 30% by weight based upon the combined weight of the abrasive grit and inorganic filler.

In molding compositions, the aggregate constitutes the major constituent and the binder constitutes a relatively minor amount. In ordinary sand type, foundry applications, the amount of binder is generally no greater than about 10% by weight and frequently within the range of about 0.5 to about 7% by weight based upon the weight of the aggregate. Most often, the binder content ranges from about 0.6 to about 5% by weight based upon the weight of the aggregate in ordinary sand type foundry shapes.

In molds and cores for precision casting application, the amount of binder is generally no greater than about 40% by weight and frequently within the range of about 5 to about 20% by weight, based upon the weight of the aggregate.

In refractories, the amount of binder is generally no greater than about 40% by weight and frequently within the range of about 5% to about 20% by weight based upon the weight of the aggregate.

In abrasive articles, the amount of binder is generally no greater than about 25% by weight and frequently within the range of about 5% to about 15% by weight based upon the weight of the abrasive material or grit.

A valuable additive to the binder compositions of the present invention in certain types of sand is a silane having the general formula:

wherein R' is a hydrocarbon radical and preferably an alkyl radical of 1 to 6 carbon atoms and R is a hydrocarbon group such as a vinyl group or at alkyl radical; an alkoxy substituted alkyl radical; or an alkyl-amine substituted aklyl radical in which the alkyl groups have from 1 to 6 carbon atoms. The aforesaid silane when employed in concentrations of about 0.05 to 2% based on the binder component of the composition improves the humidity resistance of the system.

Examples of some commercially available silanes are Dow Corning Z67040; Union Carbide A187 (gamma glycidoxy propyltrimethoxy silane); Union Carbide A1100 (gamma amino-propyltriethyxy silane); Union Carbide A1120 [N-beta (amino-ethyl)-gamma amino-propyltrimethoxy silane]; and vinyltriethoxysilane.

When the compositions of the present invention are used to prepare ordinary sand type foundry shapes, the following steps are employed:
1. Forming a foundry mix containing an aggregate (e.g. sand) and the bonding agent;
2. Introducing the foundry mix into a mold or pattern to thereby form the desired shape.
3. Allowing the shape to obtain a minimum strength in the mold; and
4. Thereafter removing the shape from the mold or pattern allowing it to further cure, thereby obtaining a hard, solid, cured foundry shape.

The foundry mix can optionally contain other ingredients such as iron oxide,, ground flax fibers, wood cereals, pitch, refractory flours, and the like.

The systems of the present invention can be used for the casting of the relatively high melting point ferrous-type metals such as iron and steel which are poured at about 2500° F., as well as for the casting of the relatively low melting point nonferrous type metals such as aluminum, copper, and copper alloys including brass.

In order to further understand the present invention, the following non-limiting examples concerned with foundry are provided. All parts are by weight unless the contrary is stated. The foundry samples are cured by the so-called "no bake" process unless the contrary is stated.

Examples 1-5 represent preparations of thermosettable polymeric cyclopentadiene derivatives of the present invention.

EXAMPLE 1

Into a 1 liter, 3-neck flask equipped with a stirrer, condenser, and thermometer, are added about 200 ml of methanol followed with good stirring by about 300 grams of cyclopentadiene and about 263 grams of paraformaldehyde. This corresponds to a mole ratio of cyclopentadiene to formaldehyde of 1 to 1.

Next, about 6 grams of 33% KOH solution in methanol are added. The reaction solution is stirred for 4 hours keeping the temperature at 15°-20° C. by cooling water as necessary. After 4 hours an additional 3.4 grams of the above KOH solution is added. After an additional hour, free formaldehyde is 0.4%. The mixture is neutralized with 3.3 grams acetic acid.

Unreacted cyclopentadiene is stripped at about 45° C. (the total distillate being about 100 grams). Vacuum is then applied and the remaining cyclopentadiene, methanol, and some water is stripped. The polymer weighs about 336 grams, is thermosettable, and has a hydroxyl number of about 315. The polymer contains dimethylene ether group linkages and hydroxymethyl terminal groups as identified by a combination of proton and $C^{13}$ magnetic resonance spectroscopy.

EXAMPLE 2

Example 1 is repeated, except that the mole ratio of cyclopentadiene to formldehyde is 1 to 2 and the amount of catalyst solution is 35% of the amount used in Example 1 based upon the moles of cyclopentadiene. The polymer obtained has a hydroxyl number of 399.

EXAMPLE 3

Into a 1 liter, 3-neck flask equipped with a stirrer, condenser, and thermometer, are added about 453.6 grams of furfuryl alcohol followed with good stirring by about 4.25 grams of a catalyst solution of 33% KOH in methanol; about 165 grams of cyclopentadiene, and about 81.5 grams of paraformaldehyde. This corresponds to a cyclopentadiene to formaldehyde mole ratio of 1:1.

Maintaining the temperature at 20° C. an identical charge of catalyst, cyclopentadiene, and paraformaldehyde is made 1, 2, and 3 hours from the initial charge. After the fourth addition, the temperature is allowed to rise to 30° C. and maintained until free formaldehyde content is less than 1%. The reaction is neutralized with 8.3 grams acetic acid and vacuum stripped at 40° C., 10-15 mm Hg, for 40 minutes. Viscosity is 510 cps, and percent non-volatiles (% N.V.) is 73.9%.

EXAMPLE 4

Example 1 is repeated, except that the mole ratio of cyclopentadiene to formaldehyde is 1 to 2.5 and the amount of catalyst solution is 71% of the amount used in Example 1 based on the moles of cyclopentadiene.

EXAMPLE 5

Example 2 is repeated, except that the reaction is terminated at a formaldehyde concentration of about 4.5%. The hydroxyl value is about 454.

EXAMPLE 6

A foundry sand mix is prepared by forming an admixture of about 60% by weight of the polymer prepared in Example 1, about 15% by weight of DBE and about 25% by weight of TXIB (Kodak). To this mixture is added about 4% by weight based upon the polymer of phenyl propyl pyridine.

The resulting composition is mixed on Wedron 510 sand in an amount of about 0.75% by weight of the sand for about 2 minutes. Next, about 0.75% by weight of the sand of a mixture containing about 75% by weight of Mondur MR and about 25% by weight of HiSol-10 is mixed on the sand for about 2 minutes. The resulting foundry sand mix is then formed into standard AFS tensile test samples using the standard procedures. The cured samples are tested for tensile strength.

The following results are obtained:

| Work Time (WT) (Mold hardness 60 psi) = 8 minutes Strip Time (ST) (Mold hardness 90 psi) = 12 minutes | |
|---|---|
| Tensile Strength | (PSI) |
| 1 hour | 100 |
| 3 hours | 253 |
| 24 hours | 100 |

EXAMPLE 7

A foundry sand mix is prepared by forming an admixture of about 37% by weight of toluene sulfonic acid, about 7.2% by weight of cupric oxide, about 13.4% by weight of water, and about 42.4% by weight of methanol. The resulting admixture in an amount of about 0.45% by weight of the sand is mixed on Wedron 510 sand for about 2 minutes. Next, about 1.5% by weight of the sand of a mixture containing about 65.6% by weight of the polymer prepared in Example 2, about 15.6% by weight of HiSol-10, about 15.6% by weight of DBE, about 3.2% by weight of isopropyl alcohol, and about 0.25% by weight of Aminosilane 1506 is mixed on the sand for about 2 minutes.

The resulting foundry sand mix is then formed into standard AFS tensile test samples using the standard procedures. The samples are cured employing a "warm box" procedure of about 350° F. with a dwell-time of about 50 seconds. The cured samples are tested for tensile strength. The following results are obtained: Tensile Strength (psi) immediate 19, after 45 minutes at room temperature 174 psi, and after 3 hours 142 psi.

EXAMPLE 8

A foundry sand mix is prepared by forming an admixture of about 37% by weight of toluene sulfonic acid, about 7.2% by weight of cupric oxide, about 13.4% by weight of water, and about 42.4% by weight of methanol. The resulting admixture in an amount of about 0.45% by weight of the sand is mixed on Wedron 510 sand for about 2 minutes. Next, about 1.5% by weight of the sand of a mixture containing about 42.7% by weight of the polymer prepared by Example 3, about 35% by weight of furfuryl alcohol, about 19.4% by weight of HiSol-10, about 2.9% by weight of isopropyl alcohol, and about 0.25% by weight of Aminosilane 1506 is mixed on the sand for about 2 minutes.

The resulting foundry sand mix is then formed into standard AFS tensile test samples using the standard procedures. The samples are cured by a "warm box" procedure using a box temperature of about 350° F. and a dwell-time of about 50 seconds. The results obtained are an immediate tensile strength of about 43 psi, after 45 minutes at room temperature a tensile strength of about 194 psi, and after 3 hours a tensile strength of about 183 psi.

EXAMPLE 9

A foundry sand mix is prepared by forming an admixture of about 75% by weight of benzene sulfonic acid and about 25% by weight of water. The resulting mixture in an amount of about 0.375% by weight of the sand is mixed on Wedron 510 sand for about 2 minutes. Next, about 1.5% by weight of the sand of a mixture containing about 41.1% by weight of the polymer prepared by Example 3, about 33.5% by weight of furfuryl alcohol, about 19.1% by weight of HiSol-10, about 2.9% by weight of isopropyl alcohol, about 0.25% by weight of Aminosilane 1506, and about 1.4% by weight of resorcinol.

The resulting foundry sand mix is then formed into standard AFS tensile test samples using the standard procedures. The cured samples are tested for tensile strength. The work time (mold hardness of about 40 psi) is about 4 minutes and the strip time (mold hardness of about 90 psi) is about 10 minutes. The tensile strength after 1 hour is about 153 psi, after 3 hours is about 283 psi, and after 24 hours is about 400 psi.

EXAMPLE 10

A foundry sand mix is prepared by forming an admixture of about 62% by weight of paratoluene sulfonic acid and about 38% by weight of water. The resulting admixture is mixed on Wedron 510 sand in an amount of about 0.45% by weight of the sand for about 2 minutes. Next, about 1.5% by weight of the sand of a mixture containing about 64.7% by weight of the polymer prepared by Example 4, about 15.4% by weight of HiSol-10, about 15.4% by weight of DBE, about 3.2% by weight of isopropyl alcohol, about 0.25% by weight of Aminosilane 1506, and about 1.4% of resorcinol is mixed on the sand for about 2 minutes. The resulting foundry sand mix is then formed into standard AFS tensile test samples using the standard procedures. The cured samples are tested for tensile strength. The work time (mold hardness of about 40 psi) is about 8 minutes and the strip time (mold hardness of about 90 psi) is about 29 minutes. The tensile strength after about 1 hour after removal from the mold is about 38 psi, after 3 hours is about 105 psi, and after 24 hours is about 207 psi.

EXAMPLE 11

A foundry sand mix is prepared by forming an admixture of about 60% by weight of the polymer prepared in Example 5, about 20% by weight of diacetone alcohol, about 19% by weight of HiSol-10, and about 1% by weight of dimethyldiethoxysilane.

The resulting composition is mixed on Wedron 510 sand in an amount of about 0.75% by weight of the sand for about 2 minutes. Next, a mixture contining about 73% by weight of Mondur MR and about 27% by weight of HiSol 10 is mixed on the sand in an amount of about 0.75% by weight of the sand for about 2 minutes.

The resulting foundry sand mix is then formed into standard AFS tensile test samples using the standard procedures. The cured sample is tested for tensile strength.

The work time (mold hardness of about 65 psi) is about 8 minutes and the strip time (mold hardness of about 90 psi) is about 10 minutes. The tensile strength after 1 hour after removal from the mold is about 212 psi, after 3 hours is about 310 psi, and after 24 hours is about 368 psi.

EXAMPLE 12

Erosion wedge cores are prepared using the compositions and curing techniques of Examples 9 and 10 hereinabove. The cores are used to have poured therein grey iron at 2700° F. and a 16-inch spru height. The castings obtained show excellent surface finish, excellent erosion resistance, and veining comparable to a zero-water, zero-nitrogen premium furan binder.

Having thus described our invention, what we claim as new and desire to secure by Letters Patent is:

1. A process for preparing a polymeric cyclopentadiene which comprises reacting cyclopentadiene, or methyl cyclopentadiene, or mixtures thereof with an aldehyde having 1–5 carbon atoms in the presence of about 0.004 to about 0.007 moles of a basic catalyst per mole of said cyclopentadiene, methyl cyclopentadiene, or both, at a temperature of about 20° C. to about 40° C.

2. The process of claim 1 wherein the time is about 4 to about 24 hours.

3. The process of claim 1 wherein about 0.1 to about 2 moles of aldehyde per mole of said cyclopentadiene are employed.

4. The process of claim 1 wherein said aldehyde is formaldehyde or acetaldehyde.

5. The process of claim 1 wherein said aldehyde is formaldehyde.

6. The process of claim 1 wherein said base catalyst is KOH.

7. A polymeric cyclopentadiene derivative obtained by the process of claim 1.

* * * * *